(12) United States Patent
Burghardt et al.

(10) Patent No.: US 7,563,837 B2
(45) Date of Patent: Jul. 21, 2009

(54) CARBODIIMIDES COMPRISING THIOCARBAMIDE ACID ESTER GROUPS

(75) Inventors: Andre Burghardt, Bobenheim-Roxheim (DE); Karl Haeberle, Speyer (DE); Ulrike Licht, Mannheim (DE); Karl-Heinz Schumacher, Neustadt (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 198 days.

(21) Appl. No.: 10/591,283

(22) PCT Filed: Mar. 4, 2005

(86) PCT No.: PCT/EP2005/002293

§ 371 (c)(1),
(2), (4) Date: Aug. 31, 2006

(87) PCT Pub. No.: WO2005/087718

PCT Pub. Date: Sep. 22, 2005

(65) Prior Publication Data

US 2007/0179226 A1 Aug. 2, 2007

(30) Foreign Application Priority Data

Mar. 9, 2004 (DE) .................. 10 2004 011 833

(51) Int. Cl.
*C08K 5/29* (2006.01)
*C07C 333/00* (2006.01)
*C07C 267/00* (2006.01)

(52) U.S. Cl. .................. 524/195; 558/232; 564/252
(58) Field of Classification Search .................. 524/195
See application file for complete search history.

(56) References Cited

U.S. PATENT DOCUMENTS 5,160,507 A * 11/1992 Horodysky .................. 44/390
5,859,166 A    1/1999 Sasaki et al.

FOREIGN PATENT DOCUMENTS

| DE | 37 20 860  | 1/1989  |
|----|------------|---------|
| DE | 195 21 500 | 6/1996  |
| DE | 199 54 500 | 5/2001  |
| DE | 100 00 656 | 7/2001  |
| EP | 0 937 563  | 8/1999  |
| EP | 0 952 146  | 10/1999 |

* cited by examiner

*Primary Examiner*—Marc S. Zimmer
*Assistant Examiner*—John Uselding
(74) *Attorney, Agent, or Firm*—Oblon, Spivak, McClelland, Maier & Neustadt, P.C.

(57) ABSTRACT

Thiocarbamides comprising at least one carbodiimide group and at least one thiocarbamic ester group of the formula

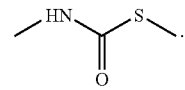

22 Claims, No Drawings

CARBODIIMIDES COMPRISING THIOCARBAMIDE ACID ESTER GROUPS

The invention relates to thiocarbamides comprising at least one carbodiimide group and at least one thiocarbamic ester group of the formula

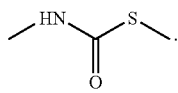

The invention also relates to the use of the thiocarbamides as a crosslinker or stabilizer.

Organic carbodiimides and their use as additives to aqueous polymer dispersions are known. They are added to polymer dispersions, for example, in order to increase the molecular weight of the polymers. In order to be able to disperse the carbodiimides easily and homogeneously in the dispersion they are provided with hydrophilic groups.

According to DE-A-10 000 656 carbodiimides comprising isocyanate groups are reacted with hydroxy carboxylic acids. A disadvantage here is that the starting compounds must be reacted in an anhydrous environment, since otherwise there is unwanted wanted competition for the isocyanate groups between the OH groups of the hydroxy carboxylic acids and the water. This means that inorganic bases cannot be used to neutralize the carboxyl groups, since the salts obtained do not dissolve in the reaction medium. It is therefore necessary to use bases which result in salts that are soluble in the reaction medium; such salts are, generally, tertiary amines. The use of tertiary amines, however, is undesirable for reasons of toxicology and odor nuisance.

DE 19 954 500 discloses carbodiimides which have been hydrophilicized with amino carboxylic acids.

These compounds exhibit inadequate adhesion properties when used as crosslinkers for adhesive dispersions, for example.

The object of the invention was to provide carbodiimides which are suitable for crosslinking polymer dispersions, do not mandatorily contain tertiary amines and have crosslinking properties improved over the prior art.

Accordingly the thiocarbamides defined at the outset and their use have been found.

The thiocarbamides of the invention comprise at least one carbodiimide group and at least one thiocarbamic ester group.

Carbodiimide groups are easily obtainable from two isocyanate groups with elimination of carbon dioxide:

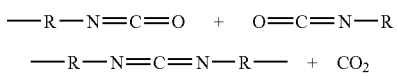

Starting from polyisocyanates, or diisocyanates, it is possible in this way to obtain carbodiimides having two or more carbodiimide groups and, if appropriate, isocyanate groups, especially terminal isocyanate groups.

Thiocarbamic ester groups have the formula

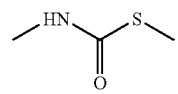

and are obtainable by reacting isocyanate groups with mercapto groups (S—H).

The thiocarbamides of the invention preferably contain hydrophilic groups.

In particular the thiocarbamides are soluble in water or dispersible in water as a result of the hydrophilic groups they contain.

Suitable hydrophilic groups include not only ionic groups but also nonionic hydrophilic groups.

The term "ionic groups" should also be taken to include groups which can be converted into ionic groups.

Mention may be made in particular of acid groups, such as carboxylic acid, sulfonic acid, phosphoric acid and phosphonic acid groups, and their salts, i.e. carboxylates, sulfonates, phosphates and phosphonates.

Nonionic hydrophilic groups are, for example, polyalkylene oxide groups or polyvinylpyrrolidone groups. The alkylene oxide units in the polyalkylene oxide groups can be, for example, ethylene oxide, propylene oxide or mixtures of the two. Preference is given to ethylene oxide.

Suitable polyalkylene oxide groups or polyvinylpyrrolidone groups for sufficient hydrophilicity are those comprising preferably at least 5, more preferably at least 8 alkylene oxide units or vinylpyrrolidone units, respectively. The polyalkylene oxide groups or polyvinylpyrrolidone groups may comprise, for example, from 5 to 80 alkylene oxide or vinylpyrrolidone units.

The thiocarbamides comprise preferably from 0.01 to 2 mol/kg, more preferably from 0.5 to 1.8 mol/kg, of hydrophilic groups, based on the weight of the thiocarbamides.

The weight fraction of the hydrophilic groups, in particular of the nonionic hydrophilic groups, is in general between 1 to 30% by weight, based on thiocarbamides.

The fraction of carbodiimide groups is generally from 0.05 to 8, preferably from 0.10 to 5, mol/kg, based on the weight of the thiocarbamides.

The carbodiimide units in the thiocarbamides of the invention are essentially formed by the coming together of 2 NCO groups with elimination of carbon dioxide to form one carbodiimide units.

The thiocarbamides comprise preferably at least one carbodiimide unit, more preferably more than one carbodiimide units; with particular preference the average degree of condensation (numerical average), i.e., the average number of carbodiimide units in the carbodiimides of the invention, is from 1 to 20, in particular from 2 to 15.

The thiocarbamides of the invention are preferably obtainable by reacting a) carbodiimides having at least one isocyanate group, b) mercapto compounds having at least one mercapto group, and c) if appropriate, further compounds having isocyanate groups or isocyanate-reactive groups.

The carbodiimides a) are obtainable as described above from polyisocyanates. Suitable polyisocyanates include, in particular, diisocyanates $X(NCO)_2$, where X is an aliphatic hydrocarbon radical having 4 to 12 carbon atoms, a cycloaliphatic or aromatic hydrocarbon radical having 6 to 15 carbon atoms or an araliphatic hydrocarbon radical having 7 to 15 carbon atoms. Examples of such diisocyanates are tetramethylene diisocyanate, hexamethylene diisocyanate, dodecamethylene diisocyanate, 1,4-diisocyanatocyclohexane, 1-isocyanato-3,5,5-trimethyl-5-isocyanatomethylcyclohexane (IPDI), 2,2-bis(4-isocyanatocyclohexyl)propane, trimethylhexane diisocyanate, 1,4-diisocyanatobenzene, 2,4-diisocyanatotoluene, 2,6-diisocyanatotoluene, 4,4'-diisocyanatodiphenylmethane, 2,4'- diisocyanatodiphenylmethane, p-xylylene diisocyanate, tetramethylxylylene diisocyanate (TMXDI), the isomers of bis(4-isocyanatocyclohexyl)methane (HMDI) such as the trans/trans, the cis/cis and the cis/trans isomers, and mixtures of these compounds.

Preference is given to aliphatic or araliphatic $C_4$ to $C_{20}$ polyisocyanates or diisocyanates.

Particular preference is given to TMXDI.

The mercapto compounds b) are compounds having at least one mercapto group, preferably having one or two mercapto groups, more preferably having one mercapto group.

The compounds b) are preferably low molecular weight compounds with a molar weight of from 90 to 1000, in particular from 90 to 500 g/mol.

The mercapto compounds preferably also have at least one, in particular one or two, more preferably one hydrophilic group.

In particular, then, the thiocarbamides have the above-indicated hydrophilic group content by virtue of mercapto compounds b). The hydrophilic groups in the mercapto compounds are, consequently, the ionic or hydrophilic nonionic groups listed above.

Preferred mercapto compounds are mercapto acids such as mercaptocarboxylic, -sulfonic or -phosphonic acids, more preferably mercaptocarboxylic or -sulfonic acids.

Examples of such include the following:

Mercaptoacetic acid, 2- and 3-mercaptopropionic acid, mercaptosuccinic acid, mercaptoethanesulfonic acid, 2- and 3-mercaptopropanesulfonic acid.

Mercapto compounds having cationic groups are, for example, mercapto amines having tertiary amino groups, e.g., dialkylaminothiols such as 2-dimethylamino-1-ethanethiol, 3-diethylamino-1-propanethiol, etc.

Mercapto compounds having nonionic hydrophilic groups are, for example, mercapto-bearing polyalkylene oxides or polyvinylpyrrolidones. Besides the mercapto groups and hydrophilic groups, the mercapto compounds may bear further isocyanate-reactive groups, e.g., hydroxyl groups or amino groups. Examples that may be mentioned include cysteine and homocysteine.

In particular the mercapto compounds b) are aliphatic compounds.

Compounds c) may be any desired polyisocyanates without carbodiimide groups or compounds having isocyanate-reactive groups.

Suitable polyisocyanates, in addition to those listed above, include aromatic polyisocyanates and polyisocyanates having more than two isocyanate groups.

Compounds having isocyanate-reactive groups are, for example, hydroxyl compounds or amino compounds, e.g., alkanediols, aliphatic diamines, alkanolamines, etc.

In general the fraction of components (c), based on the fraction of all components (a) to (c) used to prepare the thiocarbamides, is not more than 0 to 40%, preferably 0 to 30%, by weight, more preferably less than 10% by weight, in particular less than 5% by weight.

The presence of component c) is not mandatory for the purposes of the present invention, and component c) may therefore be omitted entirely.

The preparation of the thiocarbamides of the invention takes place essentially by means of two reaction steps, by
I. preparing carbodiimides having terminal isocyanate groups, by carbodiimidizing some of the isocyanate groups of component (a), and
II. reacting the compounds having terminal isocyanate groups, prepared in step I, with component (b) and, if appropriate, component (c).

In step I carbodiimide structures are produced by conventionally reacting the isocyanate groups with one another with elimination of carbon dioxide in the presence of customary catalysts known for this reaction. In step II the carbodiimides and, if appropriate, further polyisocyanates are reacted conventionally with isocyanate-reactive compounds in order to prepare thiocarbamic ester structures and, if appropriate, urethane and/or urea structures.

The molar ratio of the NCO groups to the sum of the isocyanate-reactive groups is usually from 10:1 to 0.2:1, preferably from 5:1 to 0.5:1.

Alternatively the carbodiimides of the invention can be obtained by first reacting polyisocyanates with components (b) and, if appropriate, (c), the ratio of the isocyanate groups used to the sum of the isocyanate-reactive groups being at least 2:1, and then reacting the reaction product, carrying isocyanate groups, in the presence of catalysts and with evolution of carbon dioxide, to form carbodiimides. In accordance with this version of the process initially up to 50% by weight, preferably up to 25% by weight, of the isocyanate groups of the polyisocyanates are reacted with isocyanate-reactive compounds and thereafter the free isocyanate groups are reacted wholly or partly, in the presence of catalysts and with evolution of carbon dioxide, to form carbodiimide groups.

The reactions can be carried out with preference in the presence of a solvent. Particularly suitable solvents are compounds which are good solvents for the reaction products of the reaction of step I and are also miscible with water, examples being propanone, tetrahydrofuran, dioxane, N-methylpyrrolidone, dimethylformamide, dimethylacetamide and/or propylene carbonate. It is preferred to use solvents having a boiling point at 1013 mbar of less than 100° C.

The process step in which the carbodiimide groups are formed can be carried out at elevated temperatures, e.g., at temperatures from 50 to 200° C., preferably from 150 to 185° C., advantageously in the presence of catalysts. Catalysts which have proven ideally suitable include, for example, phosphorus compounds, which are preferably selected from the group consisting of phospholenes, phospholene oxides, phospholidines and phospholine oxides. When the reaction mixture has the desired NCO group content, the formation of polycarbodiimide is normally ended. For that purpose the catalysts can be distilled off under reduced pressure or deactivated by adding a deactivator, such as phosphorus trichloride. The catalysts may also remain in the product. Polycarbodiimide preparation can additionally be carried out in the absence or presence of solvents which are inert under the reaction conditions.

If polyisocyanate is first reacted to a carbodiimide containing isocyanate groups (step I), then the intermediate formed in step I preferably has an NCO content of from 1 to 18% by weight.

Through an appropriate choice of the reaction conditions, such as the reaction temperature, type of catalyst and amount of catalyst, for example, and also the reaction time it is possible for the skilled worker to adjust the degree of condensation in the usual way. The course of the reaction is most easily followed by determining the NCO content. Other parameters as well, such as viscosity increase, color deepening or $CO_2$ evolution, can be employed for following the course of, and controlling, the reaction.

The temperature in the step in which the thiocarbamic ester groups and, if appropriate, urethane groups and urea groups are formed is normally from 10 to 100° C.

The thiocarbamides of the invention are especially suitable for increasing the molecular weight of polymers in the form of an aqueous dispersion or solution. Aqueous dispersions are preferred.

Suitable polymers include virtually all film-forming polymers.

In one preferred embodiment the polymers carry carboxyl groups, generally in amounts of from 0.01 to 2 mol/kg of polymer, preferably from 0.05 to 2 mol/kg.

Suitable polymers are, for example, water-dispersible polyurethanes. Polyurethanes of this kind and the dispersions comprising them are common knowledge.

Polyurethanes of this kind are preferably synthesized from

IIa) diisocyanates having 4 to 30 carbon atoms,
IIb) diols of which
   IIb1) from 10 to 100 mol %, based on the total amount of the diols (IIb), have a molecular weight of from 500 to 5000 and
   IIb2) from 0 to 90 mol %, based on the total amount of the diols, have a molecular weight of from 60 to 500 g/mol,
IIc) monomers other than the monomers (IIa) and (IIb) and having at least one isocyanate group or at least one isocyanate-reactive group, and further carrying at least one hydrophilic group or one potentially hydrophilic group whereby the polyurethanes are made dispersible in water,
IId) if appropriate, further, polyvalent compounds, other than the monomers (IIa) to IIc), having reactive groups which are alcoholic hydroxyl groups, primary or secondary amino groups or isocyanate groups, and
IIe) if appropriate, monovalent compounds, other than the monomers (IIa) to (IId), having a reactive group which is an alcoholic hydroxyl group, a primary or secondary amino group or an isocyanate group.

Suitable monomers (IIa) include the aliphatic or aromatic diisocyanates commonly used in polyurethane chemistry. Preference is given to the monomers (IIa) or mixtures thereof which are also mentioned as monomers (IIa) in DE-A-19521500.

Suitable monomers (IIb) and (IId) are preferably those specified as monomers (IIb) and (IId) in DE-A-19521500.

Monomers IIb1 are, for example, polyester diols or polyether diols.

The monomers IIb2 are, for example, aliphatic diols having 2 to 12 carbon atoms, e.g., 1,4-butanediol or 1,6-hexanediol.

Examples of suitable monomers (IId) include aliphatic amines having 2 to 12 carbon atoms and from 2 to 4 groups selected from the group consisting of primary or secondary amino groups. Examples are ethylenediamine, isophoronediamine or diethylenetriamine.

In order to render the polyurethanes dispersible in water they are synthesized not only from components (IIa), (IIb) and (IId) but also from monomers (IIc), different than components (IIa), (IIb) and (IId), which carry at least one isocyanate group or at least one isocyanate-reactive group and, furthermore, at least one hydrophilic group or one group which can be converted into a hydrophilic group. The term "hydrophilic groups or potentially hydrophilic groups" is abbreviated in the text below to "(potentially) hydrophilic groups". The (potentially) hydrophilic groups react with isocyanates significantly more slowly than do the functional groups of the monomers which serve to synthesize the main chain of the polymer.

Preferred monomers (IIc) are likewise those identified as monomers (IIc) in DE-A-19521500.

The fraction of the components having (potentially) hydrophilic groups as a proportion of the total amount of components (IIa), (IIb), (IIc), (IId) and (IIe) is generally such that the molar amount of the (potentially) hydrophilic groups, based on the amount by weight of all monomers (a) to (e), is from 80 to 1200, preferably from 100 to 1000 and more preferably from 150 to 800 mmol/kg.

The (potentially) hydrophilic groups can be nonionic hydrophilic groups, e.g., polyethylene oxide groups, or, preferably, (potentially) ionic hydrophilic groups, e.g., carboxylate or sulfonate groups. It is preferred to operate without effective amounts of nonionic groups.

The amount of nonionic hydrophilic groups, if such are incorporated, is generally up to 5%, preferably up to 3%, more preferably up to 1% by weight, based on the amount by weight of all monomers (IIa) to (IIe).

Monomers (IIe), used additionally if appropriate, are monoisocyanates, monoalcohols and mono-primary and -secondary amines. In general their proportion is not more than 10 mol %, based on the total molar amount of the monomers. These monofunctional compounds normally carry further functional groups such as carbonyl groups and serve for introducing into the polyurethane functional groups which allow the polyurethane to be dispersed and/or crosslinked or to undergo further polymer-analogous reaction.

Within the field of polyurethane chemistry it is common knowledge as to how the molecular weight of the polyurethanes can be adjusted through the choice of the proportions of the coreactive monomers and the arithmetic mean of the number of reactive functional groups per molecule.

Normally the components (IIa) to (IIe) and their respective molar amounts are chosen such that the ratio A:B, where A) is the molar amount of isocyanate groups and
B) is the sum of the molar amount of the hydroxyl groups and the molar amount of the functional groups which are able to react with isocyanates in an addition reaction, is from 0.5:1 to 2:1, preferably from 0.8:1 to 1.5, more preferably from 0.9:1 to 1.2:1. With very particular preference the ratio A:B is as close as possible to 1:1.

The monomers (IIa) to (IIe) employed carry on average usually from 1.5 to 2.5, preferably from 1.9 to 2.1, more preferably 2.0 isocyanate groups and/or functional groups which are able to react with isocyanates in an addition reaction.

The various preparation methods for the polyurethanes are common knowledge and are described in more detail, for example, in DE-A-19807754.

Additionally the polymers may be those obtainable by free-radical addition polymerization of ethylenically unsaturated compounds (monomers) (polyadduct for short).

Polyadducts of this kind are generally synthesized from

IIIa) from 30 to 100% by weight of principal monomers selected from $C_1$ to $C_{20}$ alky(meth)acrylates, vinyl esters of carboxylic acids comprising up to 20 carbon atoms, vinylaromatics having up to 20 carbon atoms, ethylenically unsaturated nitriles, vinyl halides and aliphatic hydrocarbons having 2 to 8 carbon atoms and 1 or 2 double bonds,
IIIb) from 0 to 20%, preferably from 0.01 to 20% by weight of a carboxylic acid having an olefinic double bond, and
IIIc) from 0 to 20% by weight of free-radically polymerizable monomers other than (IIIa) and (IIIb).

Examples of monomers (IIIa) include (meth)acrylic acid alkyl esters with a $C_1$-$C_{10}$ alkyl radical, such as methyl methacrylate, methyl acrylate, n-butyl acrylate, ethyl acrylate and 2-ethylhexyl acrylate.

In particular, mixtures of the (meth)acrylic acid alkyl esters are also suitable.

Vinyl esters of carboxylic acids having 1 to 20 carbon atoms are, for example, vinyl laurate, vinyl stearate, vinyl propionate and vinyl acetate.

Suitable vinylaromatic compounds include vinyltoluene, alpha- and p-methylstyrene, alpha-butylstyrene, 4-n-butyl-styrene, 4-n-decylstyrene and, preferably, styrene.

Examples of nitriles are acrylonitrile and methacrylonitrile.

The vinyl halides are ethylenically unsaturated compounds substituted by chlorine, fluorine or bromine, preferably vinyl chloride and vinylidene chloride.

Nonaromatic hydrocarbons having 2 to 8 carbon atoms and one or two olefinic double bonds that may be mentioned include butadiene, isoprene and chloroprene, and also ethylene, propylene and isobutylene.

The monomers (IIIa) are also preferably used in a mixture.

Vinylaromatic compounds such as styrene are, for example, frequently used in a mixture with $C_1$-$C_{20}$ alkyl(meth)acrylates, in particular with $C_1$-$C_8$ alkyl(meth)acrylates, or with nonaromatic hydrocarbons such as isoprene or preferably butadiene.

Suitable monomers (IIIb) include preferably (meth)acrylic acid or maleic acid.

Examples of suitable monomers (IIIc) include the following: esters of acrylic and methacrylic acid with alcohols having 1 to 20 carbon atoms comprising at least one further heteroatom other than the oxygen in the alcohol group and/or comprising an aliphatic or aromatic ring, such as 2-ethoxyethyl acrylate, 2-butoxyethyl(meth)acrylate, dimethylaminoethyl(meth)acrylate, diethylaminoethyl(meth)acrylate, (meth)acrylic acid aryl, alkaryl or cycloalkyl esters, such as cyclohexyl(meth)acrylate, phenylethyl(meth)acrylate, phenylpropyl(meth)acrylate or acrylic esters of heterocyclic alcohols such as furfuryl(meth)acrylate.

Further suitable monomers as monomer (IIIc) include those with amino or amide groups such as (meth)acrylamide, and also their derivatives substituted on the nitrogen by $C_1$-$C_4$ alkyl.

Of particular significance as monomers (IIIc) are hydroxy-functional monomers, examples being (meth)acrylic acid $C_1$-$C_{15}$ alkyl esters which are substituted by one or two hydroxyl groups. Particularly significant hydroxy-functional comonomers are (meth)acrylic acid $C_2$-$C_8$ hydroxyalkyl esters, such as n-hydroxyethyl, n-hydroxypropyl or n-hydroxybutyl(meth)acrylate.

The preparation of the polymer (PIII) is by free-radical addition polymerization. Suitable polymerization methods, such as bulk, solution, suspension or emulsion polymerization, are known to the skilled worker.

Preferably the copolymer is prepared by solution polymerization with subsequent dispersion in water or, with particular preference, by emulsion polymerization.

With particular preference, therefore, the polymer in question is an emulsion polymer.

In the course of emulsion polymerization, as is usual, the comonomers can be polymerized in the presence of a water-soluble initiator and of an emulsifier at preferably 30 to 95° C.

Suitable initiators are, for example, sodium, potassium and ammonium persulfate, tertbutyl hydroperoxides, water-soluble azo compounds or else redox initiators.

Examples of emulsifiers used include alkali metal salts of relatively long-chain fatty acids, alkyl sulfates, alkylsulfonates, alkylated arylsulfonates or alkylated biphenyl ether sulfonates. Further suitable emulsifiers include reaction products of alkylene oxides, particularly of ethylene oxide or propylene oxide, with fatty alcohols, fatty acids or phenols, and/or alkylphenols.

In the case of aqueous secondary dispersions the copolymer is first prepared by solution polymerization in an organic solvent and is then dispersed in water, without using an emulsifier or dispersing assistant, with the addition of salt formers, e.g., of ammonia, to copolymers containing carboxylic acid groups. The organic solvent can be removed by distillation. The preparation of aqueous secondary dispersions is known to the skilled worker and described for example in DE-A-37 20 860.

In order to adjust the molecular weight it is possible to use regulators. Suitable examples include —SH-comprising compounds such as mercaptoethanol, mercaptopropanol, thiophenol, thioglycerol, ethyl thioglycolate, methyl thioglycolate and tert-dodecyl mercaptan; they can be used additionally in amounts for example of from 0 to 0.5% by weight, based on the copolymer.

The identity and amount of the comonomers is preferably chosen so that the resulting copolymer has a glass transition temperature of from −60 to +140° C., preferably from −60 to +100° C. The glass transition temperature of the copolymer is determined by differential thermoanalysis or Differential Scanning Calorimetry in accordance with ASTM 3418/82.

The polymers may additionally comprise a water-dispersible polyester which carries carboxyl groups.

The water-dispersible polyesters which carry carboxyl groups are known for example from Encyclopedia of Polymer Science and Engineering, John Wiley & Sons, second edition, volume 12, pages 300 to 313.

The aqueous dispersions or solutions comprising the polymer normally have a solids content of from 10% to 70% by weight.

Mixtures of thiocarbamides and aqueous dispersions and/or solutions of the polymer contain thiocarbamides and polymer preferably in a weight ratio of from 0.005:1 to 1:1.

The addition of the thiocarbamides to polymer dispersions or solutions is not critical and may for example be performed by stirring into the aqueous dispersions comprising polymer. The addition may be made at any point in time prior to use thereof. The mixtures obtained are stable on storage.

The mixtures of the invention comprising thiocarbamides and polymer may comprise commercially customary auxiliaries and additives such as wetting agents, defoamers, flatting agents, emulsifiers, thickeners and thixotropic agents, and colorants such as dyes and pigments.

They are suitable, for example, for the adhesive bonding or coating of various substrates such as wood, metal, plastic, paper, leather or textile, for the impregnation of textiles and for the production of moldings and printing inks.

The dispersions of the invention can be processed by the methods which are commonplace in the adhesive, leather or coatings industry; in other words, by spraying, rolling or knife coating the dispersions onto the substrate and then drying the coated substrate.

Where the dispersions of the invention are processed as adhesives, the coated workpieces are joined to another workpiece, preferably with application of pressure, either before the dispersion film has dried or after drying.

Particularly firm adhesive bonds are obtained if workpieces which have been provided with a dried film of adhesive are heated to a temperature of about 50 to 100° C. immediately before, during or after joining.

The adhesive bonds produced by these methods are notable in particular for their storage stability and high thermal stability.

The thiocarbamides can also be used for producing adhesive films. For this purpose, aqueous dispersions comprising, for example, a polyurethane or polyadduct are blended with thiocarbamides and, if appropriate, with further auxiliaries. This mixture is applied by the customary aforementioned methods to polymeric films, preference being given to corona-treated polyethylene film. The quantities applied are normally from 5 to 6 g/m².

Coated adhesive film, comprising corona-treated polyethylene film for example, are suitable for sticking to articles of all kinds. If a polymer is used which is suitable as a pressure-sensitive adhesive, the coated film has the particular feature that it can be parted from the substrate without residue.

Adhesive films of this kind are therefore particularly suitable for producing labels or for use as protective films in order to protect articles, particularly those having sensitive surfaces such as painted surfaces or articles of plexiglass, polycarbonate or glass, e.g., screens or windows, against mechanical damage, e.g., scratching, or other environmental effects in the course of storage and transit. They further possess the advantage of having good tack; in other words, the film adheres to the substrate on mere contact, without application of high force, e.g., by laying on with the hand or by placement of the film, and can be peeled from the substrate again with moderate force (for example, applying from 1.25 to 2.5 N for an adhesive strip having a width of 25 mm).

Additionally the thiocarbamides are also suitable as a stabilizer for polymers containing ester or amide groups.

A particular advantage is the storage stability of the polymer dispersions or solutions comprising thiocarbamides and the high performance properties when used as an adhesive, such as high peel strength and good thermal stability, for example.

EXPERIMENTAL SECTION

1. Hydrophilic Carbodiimides 1.1. Preparation of a Hydrophilic Carbodiimide having Thiocarbamic Ester Groups (Inventive)

471 g of an NCO-terminated carbodiimide of TMXDI with an NCO content of 7.8% by weight were dissolved in 800 g of acetone and the solution was heated to 45° C. With stirring, a mixture of 40 g of NaOH, 73.7 g of mercaptoacetic acid, 320 g of water and 200 g of acetone was added. After 6 minutes of stirring, the mixture was diluted with 700 g of water and the acetone was stripped off under reduced pressure.

This gave a colloidal aqueous solution of a carbodiimide with a solids content of 36.4%, a pH of 10.8 and an LT of 100.

1.2. Preparation of a Hydrophilic Carbodiimide having Urea Groups (Comparative, by the Teaching of DE 19 954 500)

471 g of an NCO-terminated carbodiimide of TMXDI with an NCO content of 7.8% by weight were dissolved in 800 g of acetone and the solution was heated to 45° C. With stirring, a mixture of 40 g of NaOH, 60.0 g of glycine, 320 g of water and 200 g of acetone was added. After 6 minutes of stirring, the mixture was diluted with 700 g of water and the acetone was stripped off under reduced pressure.

This gave a colloidal aqueous solution of a carbodiimide with a solids content of 36.8%, a pH of 12.7 and an LT of 100.

2. Preparation of a Polyurethane Dispersion

Abbreviations:
DMPA: Dimethylolpropionic acid
DBTL: Dibutyltin dilaurate
IPDI: Isophorone diisocyanate 23.8 kg (9.6 mol) of a polyesterol formed from adipic acid and butane-1,4-diol with an OH number of 45.2, 0.429 kg (3.2 mol) of DMPA, 0.008 kg of DBTL and 3.2 kg of acetone were heated to 60° C. in a stirred vessel. 3.59 kg (16.2 mol) of IPDI were added and the mixture was reacted at 90° C. for 3 hours. It was then diluted with 29 kg of acetone, during which the temperature was lowered to 30° C. Subsequently a solution of 0.23 kg (2.88 mol) of NaOH in 0.23 kg of water was added. Five minutes thereafter 0.16 kg of a 50% strength by weight solution of an NCO-terminated carbodiimide of TMXDI with an NCO content of 7.8% by weight in acetone and subsequently 1.2 kg of a 50% strength by weight aqueous solution of the sodium salt of 2'-aminoethyl-2-aminoethanesulfonic acid were added. Four minutes thereafter the batch was dispersed with 42 kg of water and the acetone was then stripped off under reduced pressure.

This gave an aqueous polyurethane dispersion with a solids content of 39.2%, a pH of 7.9 and a viscosity at 250 s$^{-1}$ of 160 mPas.

3. Testing as Thermal Laminating Adhesives

For testing as thermal laminating adhesives 100 parts of the polyurethane dispersion were mixed with 100 parts of Airflex EP 17 (a dispersion of a copolymer of vinyl acetate and ethylene) and 10 parts of the crosslinker from example 1.1. and 1.2. The mixture was applied to an automotive ABS molding and dried at 23° C. for 1 h. After drying, a PVC film which is customary for industrial automotive lamination is laminated on in a heated press under 1 bar with a film temperature of 60° C.

The bonded moldings of ABS and PVC film are 50 mm wide and 150 mm long, the bond being made over a length of approximately 12 cm, leaving 3 cm of film unbonded. They were stored at 23° C. for five days. Then the peel strengths were measured at 100° C.

Description of the Test Methods:

a) Peel Strength:

Roller peel test at 100° C. using a conventional tensile tester, peel angle 90°, peel speed 100 mm/min. The parameter measured is the peel force in N/50 mm.

b) Thermal Stability:

The PVC film/ABS molding laminate under test is clamped vertically with the PVC film downward into a frame, and a weight of 300 g is attached to the free, unbonded PVC end so that under the weight the film bends vertically downward up to the point where it is bonded to the ABS. The test specimen is heated to 80° C. and a measurement is made of the distance by which the film has parted from the ABS, starting from the beginning of the bond (reported in mm).

Peel Strength:
Carbodiimide with thiocarbamic ester group: 34 N/50 mm
Carbodiimide with urea group: 24 N/50 mm
The thermal stability was measured as well.
Thermal stability (running distance at 80° C. in mm):
Carbodiimide with thiocarbamic ester group (example 1.1., inventive): 4 mm
Carbodiimide with urea group (example 1.2., non-inventive): 13 mm

The invention claimed is:

1. A thiocarbamide comprising at least one carbodiimide group and at least one thiocarbamic ester group of the formula

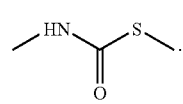

2. The thiocarbamide according to claim 1, further comprising hydrophilic groups.

3. The thiocarbamide according to claim 1, wherein the hydrophilic groups are selected from ionic groups or nonionic hydrophilic groups.

4. The thiocarbamide according to claim 3, wherein the hydrophilic groups comprise the nonionic groups, and wherein the nonionic groups are polyalkylene oxide groups.

5. The thiocarbamide according to claim 1, wherein the thiocarbamide is obtained by a process comprising reacting a) carbodiimides having at least one isocyanate group, b) mercapto compounds having at least one mercapto group, and c) optionally, additional compounds having isocyanate groups or isocyanate-reactive groups.

6. The thiocarbamide according to claim 5, wherein the carbodiimides a) are synthesized from aliphatic or araliphatic C4 to C20 polyisocyanates.

7. The thiocarbamide according to claim 5, wherein the mercapto compounds b) comprise not only at least one mercapto group but also at least one hydrophilic group.

8. The thiocarbamide according to claim 1, comprising on average from 1 to 20 carbodiimide groups and from 1 to 4 thiocarbamic ester groups.

9. The thiocarbamide according to claim 1, comprising on average from 0.01 to 2 mol of hydrophilic groups per 1 kg of thiocarbamide.

10. A method of crosslinking polymers, comprising crosslinking the polymers with the thiocarbamide of claim 1.

11. A method of stabilizing polymers containing ester or amide groups, the method comprising stabilizing the polymers with the thiocarbamide of claim 1.

12. An aqueous polymer dispersion or polymer solution comprising from 0.1 to 50 parts by weight of a thiocarbamide according to claim 1 per 100 parts by weight of polymer.

13. The aqueous polymer dispersion or polymer solution according to claim 12, wherein the dispersed or dissolved polymer is a polyurethane or a polymer obtained by free-radical addition polymerization of ethylenically unsaturated compounds.

14. The aqueous polymer dispersion or polymer solution according to claim 12, wherein the dissolved or dispersed polymer contains carboxylic acid groups.

15. The aqueous polymer dispersion or polymer solution according to claim 13, wherein the dissolved or dispersed polymer contains carboxylic acid groups.

16. A method of adhering two substrates comprising applying the polymer dispersion or solution of claim 12 to at least one surface of the first substrate to form a coated substrate and, contacting the coated surface of the coated substrate with a second substrate to adhere the substrates.

17. A method of adhering substrates, comprising
providing the polymer dispersion or polymer solution of claim 12 as or in a heat-activatable adhesive,
providing the substrates with a dried film of said adhesive, and
heating the substrates immediately before, during or after joining.

18. A substrate coated, impregnated or adhesively bonded with the polymer dispersion or solution according to claim 12.

19. A substrate coated, impregnated or adhesively bonded with the polymer dispersion or solution according to claim 13.

20. A substrate coated, impregnated or adhesively bonded with the polymer dispersion or solution according to claim 14.

21. A method of coating a substrate comprising applying the polymer dispersion or solution of claim 12 to at least one surface of substrate to coat the substrate.

22. A method of impregnating a substrate comprising impregnating the substrate with the polymer dispersion or solution of claim 12.

* * * * *